United States Patent [19]
Krause

[11] Patent Number: 6,131,442
[45] Date of Patent: Oct. 17, 2000

[54] METHOD OF WOOD CHIP MOISTURE ANALYSIS

[75] Inventor: Andrew M. Krause, Clintonville, Wis.

[73] Assignee: Riverwood International Corporation, Atlanta, Ga.

[21] Appl. No.: 09/363,910

[22] Filed: Jul. 28, 1999

[51] Int. Cl.[7] .......................... G01N 25/56; G01N 25/60; G01N 5/02; G01N 5/00

[52] U.S. Cl. ................................. 73/73; 73/76; 73/29.1; 73/29.2; 436/42

[58] Field of Search ................................ 73/73, 76, 29.1, 73/29.2; 436/42

[56] References Cited

U.S. PATENT DOCUMENTS

| | | | |
|---|---|---|---|
| 3,950,892 | 4/1976 | Simkin | 47/58 |
| 4,429,048 | 1/1984 | Scholz | 436/42 |
| 5,227,183 | 7/1993 | Aung et al. | 426/102 |
| 5,863,582 | 1/1999 | Sugisaki | 426/271 |

*Primary Examiner*—Hezron Williams

[57] ABSTRACT

A method of determining the moisture content in wood in which a sample of the wood being tested is first frozen with liquid nitrogen, homogenized and a test sample is placed in a Karl Fischer titration system. The test sample is placed into a solvent solution and the reagent or titrant is progressively added to the solvent solution as the presence of moisture from the wood sample is detected. Once the moisture has been titrated from the solution the moisture content of the wood is determined based upon the amount of reagent dispensed into the titration solution.

17 Claims, 1 Drawing Sheet

6,131,442

METHOD OF WOOD CHIP MOISTURE ANALYSIS

FIELD OF THE INVENTION

The present invention relates in general to a method of analyzing moisture content and articles. In particular, the present invention relates to a method of analyzing moisture content of wood and wood chips for pulping and paper making to enable greater control of the pulping and paper making processes.

BACKGROUND OF THE INVENTION

In the process of making paper, it is important to determine and keep close track of the moisture content of the wood being processed as the moisture content affects pulp yield during the pulping and paper making processes and thus can greatly influence the cost of pulping and paper making. For example, when wood is purchased in lots, it is generally purchased based on dry weight of the wood. Therefore, it is important to know the moisture content of the wood in order to more accurately calculate the dry weight of the wood. In addition, it is important to determine the moisture content of the wood chips being fed to the digesters along a pulping line to enable greater control of the cooking liquor being charged into the digesters and to enable greater control of the liquor/wood and chemical to wood ratios in the digesters to better control and thus lower the operating costs for the digester line.

Such moisture determinations can be made in "real-time" as the wood chips are fed to the digester using on line analyzers, such as the Micromoist Analyzer manufactured by Berthold. Such analyzers, however, must be precisely calibrated to insure accuracy in their measurements of the moisture content of the wood chips being fed to the digesters. In addition, for other applications in which the moisture content of wood and/or wood chips is determined, the processes for determining the wood chip moisture content must be carried out as efficiently and quickly as possible, preferably on site at a paper mill, to minimize the potential for variations in the calculated moisture content and actual moisture content that could occur over extended time delays due to changes in the moisture of the sampled material resulting from condensation of moisture in the sample container, diffusion of moisture out of the container, and possible stratification of moisture within the large samples required by the current methods.

There are currently two primary or standard methods for determining or calculating moisture content of wood/wood chips for use in calibrating the micromoist analyzers or meters. These include the TAPPI T208 OM-94 standard method for analyzing "Moisture in Wood, Pulp, Paper and Paperboard by Toluene Distillation", and oven drying of wood chip samples. In the first method by which moisture content in wood, pulp and paper is determined by toluene distillation, toluene, a hazardous/flammable liquid, is used to distill water out of a quantity or sample of wood chips. Since water is not miscible with toluene, a layer of water generally is formed in a receiving vessel after application of the toluene, which water can then be measured to determine the moisture content. However, this method has certain serious drawbacks or problems including toluene being a hazardous carcinogenic and highly flammable material, the use of which requires a large distillation apparatus and significant fume hood space for handling hazardous material, both of which is expensive and space intensive. This method further is very labor intensive as it requires close monitoring of the distillation continuously over a period of five or more hours needed to insure that all the water is extracted from the samples.

The second method, the oven drying method is much simpler, and typically does not require special equipment for handling hazardous materials such as fume hood space, etc. Instead, this method involves drying a measured quantity of wood chips in an oven for approximately 24 hours, taking measurements from the samples both before and after drying to determine amount of moisture within the sample. A significant problem with such a method is that samples are added and removed from the oven sporadically over a 24-hour period, a moisture free environment could not be maintained which resulted in large variations in the subsets of the samples. In addition, temperature and air circulation within the oven also affects the drying rates of the samples so that some samples dried faster than others, creating variations. Further, when wood is oven dried, all the material within the wood in addition to the moisture or water in the wood that is volatile at the oven temperatures tends to evaporate, thus causing overestimation of the amount of water in the wood chips.

In addition, another significant factor with using both of these processes is that to ensure significant accuracy in developing a calibration curve for calibrating micromoist analyzers, approximately 30 moisture determinations spanning the expected range are necessary. Each of the moisture determinations generally are conducted with an average subset of approximately five samples of wood chips, such that upwards of 150 separate samples must be analyzed in order to get a substantially complete and accurate calibration curve. With such a large number of samples typically needed to insure an accurate calibration curve, the time and apparatus required for conducting these tests is significantly extensive, for example, requiring large fume hood space or large ovens and close monitoring, thus significantly increasing the cost of performing these methods. Further, given the necessity of performing such determinations as rapidly as possible to minimize the potential for variations or changes in the moisture content of the wood after sampling, i.e., from condensation of moisture from the sample to the container, diffusion of moisture out of the sample container, and possible stratification of moisture within the large samples required by the current methods, it is not practical to ship large samples of the wood chips being processed to outside laboratories due to the time and expense required for testing such a large number of samples.

Accordingly, it can be seen that a need exists for a method of determining moisture content in wood for use in a paper making process that is inexpensive to perform and which does not require extensive processing equipment and which further can be performed quickly and accurately on site at a paper mill.

SUMMARY OF THE INVENTION

Briefly described, the present invention comprises a method of determining moisture content in wood chips, which is designed to be performed on site at a paper making plant or mill and which produces an accurate determination of moisture content rapidly without requiring special handling equipment. In general, the present method utilizes a Karl Fischer titration, preferably using an automatic Karl Fischer titration unit to perform the titration automatically using a Karl Fischer titrant such as an iodine, sulfur dioxide and imidazole reagent solution with a solvent, typically anhydrous methyl alcohol or similar low moisture alcohol solvent.

As an initial step in the method of the present invention, the Karl Fischer titrant or reagent first is standardized to determine the concentration of the Karl Fischer reagent. The concentration of the reagent is determined by adding a known amount of approximately 5 grams of a moisture primary standard material such as, for example, sodium tartrate di-hydrate, typically selected having a known moisture content in a range of between approximately 14.1% to 14.5%, which is added to a receiving vessel for the automatic titrator that is filled with approximately 250 milliliters of the anhydrous methyl alcohol solvent that has been previously conditioned by the Karl Fischer titrator to remove any excess water which may be present in the solvent or receiving vessel. The Karl Fischer reagent is added by the automatic titrator until an end point is reached at which the moisture has been titrated from the sodium tartrate di-hydrate and anhydrous methyl alcohol solvent solution. The automatic titrator records the amount of reagent required to titrate out the known amount of moisture from the solution, from which the concentration of the reagent thus can be determined. Several replicate determinations generally should be performed to get a statistically valid result.

At the same time that the concentration of the Karl Fischer reagent is being initialized or determined, or shortly thereafter, a sample of approximately 2,000 to 3,000 grams of wood chips is quick frozen by applying the liquid nitrogen to the wood chips, such as, by immersing the wood chips into a bath of liquid nitrogen or pouring the liquid nitrogen over the wood chips to minimize evaporation of surface water on and/or variations in the moisture content within the wood chips after removing them from the bulk sample. Thereafter, the frozen samples are placed in a high capacity laboratory homogenizer. Typically, the homogenization of the wood chips is done for approximately one to two minutes or less to avoid heating of the sample as the wood chips are ground into a fine powder, in order to avoid a resulting loss of water. Thereafter, a known amount of approximately 1 to 1.5 gram samples of homogenized wood chips are removed to the automatic Karl Fischer titrator and are placed into the receiving vessel of the automatic titrator. The samples are received within the receiving vessel, placed into the anhydrous methyl alcohol solvent solution, with the resultant titration solution being constantly stirred by the automatic titrator.

During the titration operation, additions of the Karl Fischer reagent are made automatically by the automatic titrator as the presence of moisture is detected or such as through a coulometric measurement of an electrochemical reaction in the titration solution. The Karl Fischer titrant is added automatically by the Karl Fischer titrator until it is detected that less than approximately 25 microliters of reagent are being added to the titration solution over an averaged approximately one minute time frame, which indicates that an end point has been reached where the moisture has been substantially removed from the solution. A moisture determination for the wood chips then is calculated based upon the volume of the Karl Fischer reagent dispensed into the solution multiplied by the concentration or titer of the Karl Fischer reagent, divided by the sample weight times 100 (to change the result to % moisture) to develop the percentage of moisture within the sample of wood chips.

The entire titration process typically can be accomplished in approximately two to ten minutes. This procedure generally is repeated until enough statistical information has been obtained to determine a mean and relative percent standard deviation of each sample, typically 5 to 8 replications. In comparison tests conducted using the method of the present invention as compared to moisture determinations made using the oven drying and TAPPI method of moisture determination using toluene distillation, the method of the present invention was found to achieve comparable results but with less standard deviation in the results, and requiring considerably less time for the method to be conducted.

Various objects, features and advantages of the present invention which will become apparent to those skilled in the art upon reading the following specification, when taken in conjunction with the accompanying drawings.

DETAILED DESCRIPTION

Figure 1:
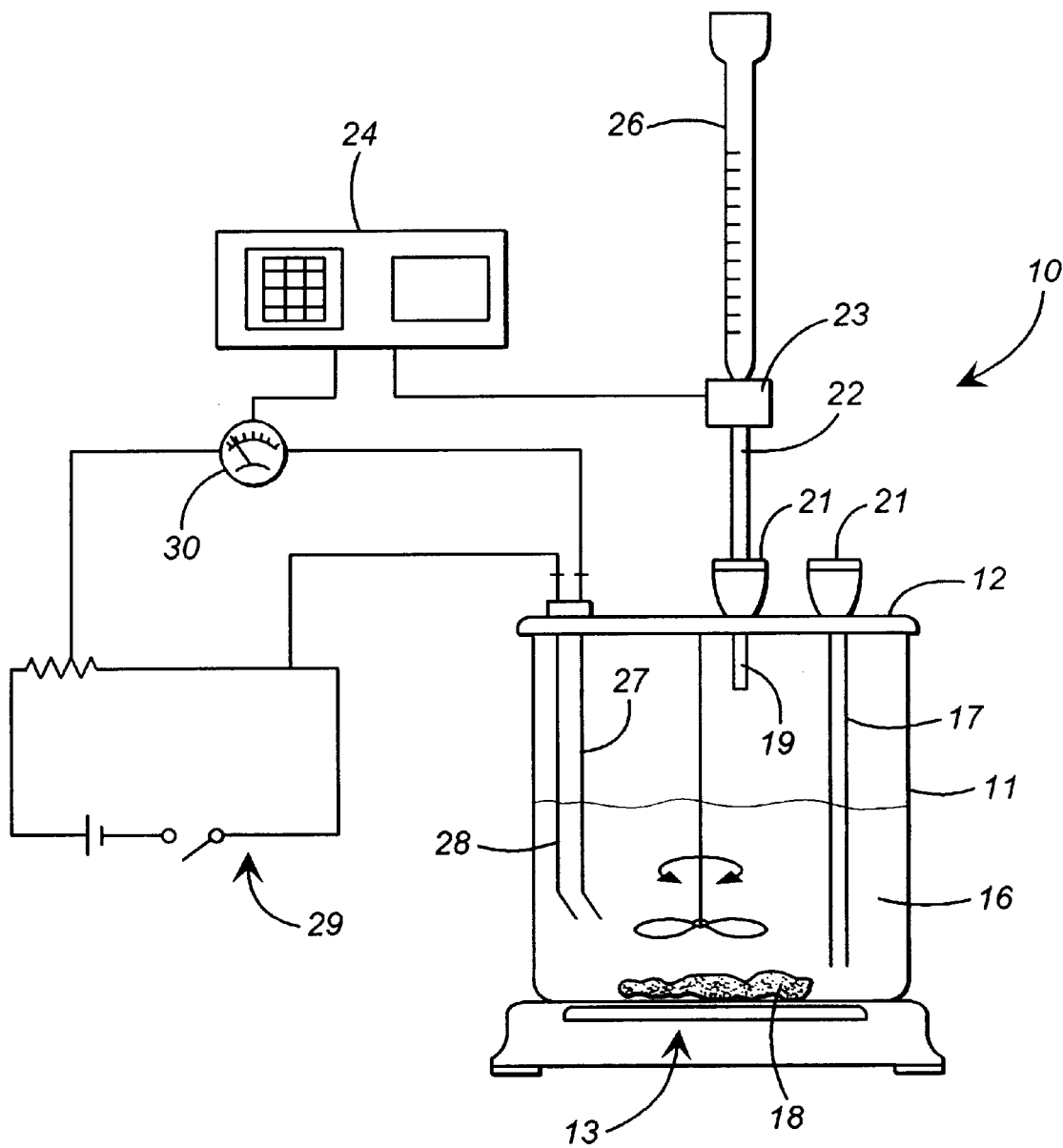
FIG. 1 schematically illustrates a Karl Fischer titration system for use with the method of the present invention.

The present invention, described in greater detail, is directed to a method of analyzing and determining the moisture content in wood, primarily for use in a paper making process at a paper mill or plant. The method of the present invention will be used for a variety of applications such as: for determining the dry weight of wood purchased by the mill; for determining the moisture content of wood chips being fed to the digesters in which the wood chips are cooked to form the wood pulp; for calibrating a series of Micromoist Analyzers to analyze the moisture content of the wood chips in real time as the chips are being fed to the digesters to enable greater control of the cooking liquor to wood ratio; or chemical to wood ratio for the digesters allowing for better control of the cooking time required for cooking the wood chips in the digesters resulting in a more uniformly cooked pulp with more consistent and predictable physical properties. Other uses for determining the moisture content of wood and wood chips at a paper mill or plant will be apparent to those skilled in the art and, by way of example, additionally could include moisture determination in finished paper products or raw or site prepared materials used in the papermaking process such as made down wet or dry strength agents, sizing agents, or clay based coatings. Any material in which moisture content is of interest could lend itself to this procedure as long as the analyzed material does not competingly react or interfere with the chemistry of the titration. The suitability of each material for the titration process must be determined on an individual basis.

The present invention generally is designed for use with a conventional automatic Karl Fischer titration unit, typically a volumetric titration unit, although a coulometric titration unit also can be used if so desired. Such automatic titration units or systems are commonly known to those skilled in the art such as the METTLER-TOLEDO Model DL35 automatic titration unit or the TURBO2® volumetric Karl Fischer titrator manufactured by Orion. It further will be understood by those skilled in the art that it also is possible to use a conventional, manual Karl Fischer titration system in which the Karl Fischer reagent is manually added through the use of a graduated burette such as with 0.10 milliliter delineation's. An example of a Karl Fischer titration system for use with the method of the present invention is schematically illustrated in FIG. 1.

As shown in FIG. 1, the Karl Fischer titration system 10 typically will include a receiving vessel 11 such as a glass beaker or container having a sealed lid 12 and a magnetic stirring mechanism 13. The magnetic stirring mechanism constantly stirs a titration solution 16 that is contained within the receiving vessel 11. The titration system 10 further includes an input tube 17 for depositing a sample of wood chips 18 within the receiving vessel, if so desired, and an input tube or port 19 for inputting a Karl Fischer titrant or reagent into the titration solution 16. The input tube or port 19 for the Karl Fischer reagent generally includes a stopper 21 through which is extended a flow tube 22 and is connected to a meter or a flow control valve 23 that is typically controlled automatically by the automatic titration system controller 24 typically a microprocessor based contrast. A reservoir such as a glass burette, illustrated at 26, with a graduated scale in approximately 0.1 milliliter increments or delineations, or simply a bottle of Karl Fischer reagent solution is connected to the flow tube via the flow control 23. Indicator or detector electrodes 27 and 28, typically formed from platinum or similar conductive material, are received within the titration solution 16 and are connected to a power supply 29 and meter or measuring unit 31 as indicated in FIG. 1. The meter and the power supply are controlled and monitored through the system controller 24, which detects a change in potential or current within the titration solution via the electrodes so as to automatically detect the presence or absence of moisture within the titration solution or automatically controlling the titration operation.

In performing the method of the present invention, a non-Pyridine containing Karl Fischer titrant or reagent will be used, typically an Imidazole-based agent such as HYDRANOL® Composite 5 manufactured by Reidel De Haenn, typically containing iodine, sulfur dioxide and Imidazole, or similar known Pyridine-free Karl Fischer reagent. The titration system generally includes a low moisture containing solvent, preferably an alcohol solvent such as anhydrous methyl alcohol or methelene in which the sample of wood chips is received to form the titration solution.

As an initial step in the method of the present invention, the Karl Fischer reagent is standardized to determine the titer or concentration of the reagent that will be used for the titration of the wood chips. The standardization of the Karl Fischer reagent is conducted by adding a desired quantity, for example, 5 grams, of a moisture standard material having known moisture range. Preferably, the moisture standard material will be a sodium tartrate di-hydrate material which is a primary moisture standard material having a moisture range of 14.1 percent to 14.5 percent. The five grams of the sodium tartrate di-hydrate are added to the receiving vessel of the automatic Karl Fischer titrator, which has been filled with approximately 250 milliliters of the anhydrous methyl alcohol solvent, with the solvent typically previously being conditioned by the automatic titrator to remove any excess water that may be present in the solvent or in the receiving vessel. The automatic titrator initially is placed in its "titer mode" as the sodium tartrate di-hydrate is added for determining the titer or concentration of the Karl Fischer reagent to be used for the titration of the wood chips.

The Karl Fischer reagent concentration determination is conducted by the automatic titrator adding the reagent to the mixture of anhydrous methyl alcohol solvent and sodium tartrate di-hydrate material at a desired rate input into the controller for the system until the system detects that an end point has been reached, at which point the moisture will have titrated out of the anhydrous methyl alcohol solvent solution. Preferably, the reagent concentration determined for titrating the known moisture standard material out of the solution should be between approximately 4.98 and 5.98 milliliters per milliliter, which concentration is automatically calculated by the titration system. This concentration determination procedure is repeated, typically for two to three additional trials or runs, to establish a good mean value of the strength or concentration of the Karl Fischer reagent. This value of the concentration of the Karl Fischer reagent is stored in the automatic titration system for use by the system in its moisture determination or mode or "KF mode".

It will further be understood by those skilled in the art that other types of moisture standard materials also can be used in place of the sodium tartrate di-hydrate, including using a known amount of approximately 500 milligrams of water that is injected directly into the receiving vessel of the automatic Karl Fischer titrator for use as a standard for determination of the reagent titer or concentration. Typically, the weight of the water is calculated to the nearest 0.0001 grams prior to starting the titrator and the water generally will be Deionized water with a resistivity of approximately 15 to 20 megaohms, preferably 18 to 19 megaohms.

As a next step or to be conducted simultaneously with the determination of the titer or concentration of the Karl Fischer reagent to be used for titrating the moisture content of the wood chips, a representative sample of approximately 2,000 to 3,000 grams of wood chips is placed into a clean, dry receiving vessel, typically made from plastic or glass. If the sample is taken from a larger grouping of materials, such as a pile of wood chips or from stacked wood, a composite of 2,000 or 3,000 grams generally will be taken from the middle of the bulk wood sample to ensure that a representative sample of wood chips is taken.

The wood chips then are subjected to an application of liquid nitrogen such as by being immersed into a Dewar container containing a bath of liquid nitrogen. It will also be apparent to those skilled in the art that liquid nitrogen further can be applied in other methods, such as by spraying or pouring the liquid nitrogen over the samples in the Dewar container. The wood chips are exposed to the liquid nitrogen for a period of approximately one to two minutes, although larger or smaller sample sizes may require longer or shorter immersion times in order to rapidly or quick freeze the wood chips. The quick freezing of the wood chips with the liquid nitrogen fixes the moisture within the wood chips and minimizes evaporation of surface water on the wood chips. This is done to minimize any potential loss or variation in the moisture content of the wood chips during the homogenization and subsampling process.

The frozen samples of wood chips then are placed in a high capacity, high torque laboratory homogenizer as is known in the art, such as are manufactured by Polytron and which typically include a blade or grinding mechanism for grinding the frozen samples into a powder. Typically, the homogenization of the samples will require less than one minute of run time, with the run time being dependent upon the sample sizes placed within the homogenizer. Preferably, the run times for the homogenization of the frozen samples of wood chips are kept at a minimum of approximately one to two minutes to avoid heating of the samples due to friction which may result in a loss of water from the samples of wood chips. Once the frozen wood chips have been homogenized into a powder, a test sample of approximately 1 to 1.5 grams of the homogenized wood chips are weighed out on an analytical balance so as to calculate the exact weight of the test sample to the nearest 0.0001 grams. Thereafter, the sample is placed in a receiving bag, which typically is an airtight plastic bag as known in the art, for transport of the sample to the automatic titration system.

The sample of homogenized wood chips is placed into the receiving vessel 11 of the automatic titration system 10, as for example through the sample input tube 17, being placed into approximately 250 ml of the anhydrous methyl alcohol solvent solution to form the titration solution. As a next step, the sample bag is weighed to check the weight difference from the original sample to that of the remaining weight of the sample bag to ensure the accuracy of the sample weight being delivered to the receiving vessel of the automatic titration system. This weight difference generally is entered as the weight of the sample within the receiving vessel into the automatic titration system's memory. The magnetic stirring mechanism 13 of the automatic titration system constantly stirs the titration solution 16 of the sample and anhydrous methyl alcohol solvent solution as the titration operation is commenced. Prior to the titration of the wood chips, the automatic titration system is placed in its moisture determination or KF (Karl Fischer) mode and the system started prior to the addition of the test sample of wood chips.

The titration procedure generally is conducted as a volumetric titration, although a coulometric procedure can be utilized as well, with the volume of the Karl Fischer reagent that is added by the automatic titration system carefully monitored. The automatic titrator generally automatically adds the Karl Fischer reagent based upon programmed rate values as the presence of moisture is detected by the electrodes. Typically, the titration rate for the addition of the Karl Fischer reagent will be between approximately 5 to 8 microliters per minute up to approximately 10 milliliters per minute with a stop volume set for the system at approximately 10 milliliters. The drift control for the automatic titration system further will be set for approximately 25 microliters per minute. The automatic titration system monitors the titration solution to detect the presence of water based upon the measuring or indicating electrodes detecting of the change in potential, which indicates whether iodine needs to be added to react with the water so that the electrode voltametrically senses when water is present.

As long as the detector electrodes detect water within the titration solution, the automatic titrator continues to dispense or release iodine in the form of the Karl Fischer reagent solution into the titration solution to react with the water. The addition of the Karl Fischer reagent continues until an end point is reached whereat the detection electrode ceases to indicate that water is present and the system detects that it is adding less than 25 microliters of Karl Fischer reagent to the receiving vessel over an averaged one minute time frame. This rate of 25 microliters over an average one minute time frame is selected as a stability factor for the titration that is programmed into the automatic titrator, and can be varied as will be known to those skilled in the art as needed to adjust the accuracy of the titration of the sample of wood chips.

The microprocessor based system control of the automatic titration system records the volume of the Karl Fischer reagent that was dispensed into the titration solution. Thereafter, based upon the concentration of iodine in the Karl Fischer reagent solution, the system automatically calculates the amount of water present in the sample of wood chips. This moisture determination is based upon the following formulation:

> Percent moisture=(((volume of Karl Fischer reagent dispensed, ml)×(reagent titer, mg water/ml reagent ))/sample weight, mg)×100(to change result to % moisture).

The % recovery or efficiency of the titration may also be calculated by performing another series of titrations with the same sample to which a known amount of moisture standard has been added. The amount added would be on the order of the same magnitude as the amount of water determined in the initial sample. Typically about 5 grams of Sodium Tartrate Di-Hydrate is added. Percent recovery is then calculated as follows:

> % Recovery=(((((volume of Karl Fischer reagent dispensed, ml–volume of Karl Fischer reagent needed to absorb the amount of water from the standard that was added, ml)×reagent titer, mg water/ml reagent)/sample weight of wood, mg)×100%)/(% moisture determined from initial sample))×100% (to change result to % recovery)

The titration operation is conducted automatically by the Karl Fischer titration system and typically takes between approximately two to ten minutes. Thereafter, the titration is repeated using additional test samples from the representative batch of sample wood chips. Such repeated titrations are used to generate a mean and standard deviation of the moisture content of the wood chips for use in various applications, such as for calibrating Micromoist Analyzers for the wood chips on a digester line. Typically, five to eight additional sample runs will be made, although fewer or greater sample replicates can be done, depending on the accuracy required by the application. Since the timing required for conducting the titrations is relatively small, a full run of multiple sample titration runs can be conducted in approximately 15 minutes to under one hour. This enables the moisture content of wood and wood chips at a paper mill to be determined on a much more rapid basis without sacrificing accuracy and therefore substantially reduces or minimizes the potential for variations occurring in the moisture content of the wood due to exposure to the elements such as rain, heat and cold, and humidity, and changes in the moisture of the sampled material due to condensation of moisture in the sample container, diffusion of moisture out of the container, and possible stratification of moisture within the large sample required by the current methods, to enable much more accurate real time measurement of the moisture content of the wood. The present system further does not require any special handling equipment such as fume hood space or large ovens and thus can be conducted on site without requiring extensive manpower to monitor and continually adjust the system for conducting the moisture determinations.

In comparison tests run on batches of test samples taken from the same bulk sample of wood chips, using the method of the present invention versus the conventional TAPPI toluene distillation and oven drying methods, the present invention provided determinations of moisture content that were compared favorably accurately to the determinations using the conventional methods and with less standard deviation than the conventional methods. The present invention further was to be conducted in a generally shorter time period and with less expense than the conventional methods. Tables summarizing the results of these tests are set forth below.

TABLE 1

Moisture Determination by Present Invention

|  | Moisture Determination |  | Mean | Std. Dev. | Rel. Std. Dev. |
|---|---|---|---|---|---|
| GROUP A | 1) | 49.68 | 49.82 | .1136 | 0.23% |
|  | 2) | 49.73 |  |  |  |
|  | 3) | 49.75 |  |  |  |
|  | 4) | 49.89 |  |  |  |
|  | 5) | 49.83 |  |  |  |

TABLE 1-continued

Moisture Determination by Present Invention

| | Moisture Determination | | Mean | Std. Dev. | Rel. Std. Dev. |
|---|---|---|---|---|---|
| | 6) | 50.01 | | | |
| | 7) | 49.74 | | | |
| | 8) | 49.74 | | | |
| GROUP B | 1) | 49.71 | 49.68 | .3025 | .61% |
| | 2) | 49.66 | | | |
| | 3) | 49.93 | | | |
| | 4) | 49.89 | | | |
| | 5) | 49.78 | | | |
| | 6) | 49.98 | | | |
| | 7) | 48.99 | | | |
| | 8) | 49.71 | | | |
| GROUP C | 1) | 50.01 | 49.68 | .1025 | .21% |
| | 2) | 49.87 | | | |
| | 3) | 49.88 | | | |
| | 4) | 49.95 | | | |
| | 5) | 49.88 | | | |
| | 6) | 50.11 | | | |
| | 7) | 49.94 | | | |
| | 8) | 49.77 | | | |
| GROUP D | 1) | 50.11 | 49.88 | .1503 | .30% |
| | 2) | 49.97 | | | |
| | 3) | 49.78 | | | |
| | 4) | 49.88 | | | |
| | 5) | 49.87 | | | |
| | 6) | 50.02 | | | |
| | 7) | 49.85 | | | |
| | 8) | 49.73 | | | |
| GROUP E | 1) | 49.99 | 49.92 | .1470 | .29% |
| | 2) | 49.96 | | | |
| | 3) | 49.82 | | | |
| | 4) | 49.77 | | | |
| | 5) | 49.69 | | | |
| | 6) | 49.99 | | | |
| | 7) | 50.04 | | | |
| | 8) | 50.12 | | | |

TABLE 2

Moisture Determination by Oven Drying

| | Moisture Determination | | Mean | Std. Dev. | Rel. Std. Dev. |
|---|---|---|---|---|---|
| GROUP F | 1) | 50.95 | 51.33 | .7831 | 1.5% |
| | 2) | 50.27 | | | |
| | 3) | 51.98 | | | |
| | 4) | 51.25 | | | |
| | 5) | 52.97 | | | |
| | 6) | 50.56 | | | |
| | 7) | 50.99 | | | |
| | 8) | 51.23 | | | |
| GROUP G | 1) | 51.54 | 52.72 | .9802 | 1.9% |
| | 2) | 52.98 | | | |
| | 3) | 53.23 | | | |
| | 4) | 52.99 | | | |
| | 5) | 52.41 | | | |
| | 6) | 53.98 | | | |
| | 7) | 54.00 | | | |
| | 8) | 51.65 | | | |
| GROUP H | 1) | 52.44 | 52.63 | 1.0186 | 1.9% |
| | 2) | 52.98 | | | |
| | 3) | 53.40 | | | |
| | 4) | 54.02 | | | |
| | 5) | 51.01 | | | |
| | 6) | 53.48 | | | |
| | 7) | 51.69 | | | |
| | 8) | 52.04 | | | |
| GROUP I | 1) | 52.00 | 53.24 | .7893 | 1.5% |
| | 2) | 52.43 | | | |
| | 3) | 53.10 | | | |
| | 4) | 53.99 | | | |

TABLE 2-continued

Moisture Determination by Oven Drying

| | Moisture Determination | | Mean | Std. Dev. | Rel. Std. Dev. |
|---|---|---|---|---|---|
| | 5) | 52.73 | | | |
| | 6) | 54.01 | | | |
| | 7) | 53.98 | | | |
| | 8) | 53.67 | | | |

TABLE 3

Moisture Determination by Toluene Distillation

| | Moisture Determination | | Mean | Std. Dev. | Rel. Std. Dev. |
|---|---|---|---|---|---|
| GROUP J | 1) | 49.56 | 50.61 | 1.5141 | 3.0% |
| | 2) | 49.34 | | | |
| | 3) | 50.99 | | | |
| | 4) | 50.45 | | | |
| | 5) | 51.20 | | | |
| | 6) | 48.33 | | | |
| | 7) | 53.00 | | | |
| | 8) | 51.99 | | | |
| GROUP K | 1) | 48.56 | 49.64 | .8218 | 1.7% |
| | 2) | 48.67 | | | |
| | 3) | 49.88 | | | |
| | 4) | 50.21 | | | |
| | 5) | 49.98 | | | |
| | 6) | 48.99 | | | |
| | 7) | 49.91 | | | |
| | 8) | 49.72 | | | |
| GROUP L | 1) | 50.09 | | | |
| | 2) | 50.25 | | | |
| | 3) | 51.01 | | | |
| | 4) | 49.98 | | | |
| | 5) | 49.99 | | | |
| | 6) | 49.23 | | | |
| | 7) | 49.85 | | | |
| | 8) | 49.72 | | | |
| GROUP M | 1) | 49.99 | 49.93 | .5694 | 1.1% |
| | 2) | 49.23 | | | |
| | 3) | 50.55 | | | |
| | 4) | 50.21 | | | |
| | 5) | 50.55 | | | |
| | 6) | 49.96 | | | |
| | 7) | 50.01 | | | |
| | 8) | 48.97 | | | |
| GROUP N | 1) | 50.26 | 50.26 | .8018 | 1.6% |
| | 2) | 51.34 | | | |
| | 3) | 49.67 | | | |
| | 4) | 49.82 | | | |
| | 5) | 48.98 | | | |
| | 6) | 49.99 | | | |
| | 7) | 50.98 | | | |
| | 8) | 51.01 | | | |

It will be understood by those skilled in the art that while the present invention has been disclosed above with reference to a preferred embodiment, various modifications, changes and additions can be made thereto without departing from the spirit and scope of the invention as set forth in the following claims.

What is claimed is:

1. A method of determining moisture content in wood chips, comprising the steps of:
   freezing a sample of wood chips to minimize variations in the moisture content of the wood chips;
   homogenizing the frozen sample of wood chips;
   placing a desired amount of the homogenized sample of wood chips in a solvent solution in a titration system;
   titrating the homogenized wood chips by adding a titrant solution to the solvent solution containing the wood chips as the presence of moisture is detected until a desired end point is reached; and determining the moisture content of the sample of wood chips based upon titrant concentration, amount of titrant dispensed and the amount of the sample of wood chips placed in solution.

2. The method of claim 1 and wherein the step of freezing the sample of wood chips comprises applying liquid nitrogen to the sample for a desired time depending on size of the sample.

3. The method of claim 1 and wherein the step of homogenizing the sample comprises placing the sample in a homogenizer and grinding the sample into a powder.

4. The method of claim 1 and wherein the step of titrating the homogenized sample of wood chips includes the steps of detecting a change in potential of the solvent solution as the titrant is added thereto and discontinuing the titration when the rate at which the titrant is added is less than approximately 25 microliters of titrant added over approximately a one minute time frame.

5. The method of claim 1 and further including the step of standardizing the titrant concentration, including the steps of adding a measured amount of a moisture standard material having a known moisture content to a solvent solution, dispensing the titrant into the solvent solution to titrate the moisture out of the solution, and determining the titrant concentration based upon the amount of titrant dispensed to titrate the moisture from the moisture standard material.

6. The method of claim 1 and wherein the titrant comprises a non-pyridine containing Karl Fischer reagent.

7. The method of claim 1 and wherein the solvent solution comprises an anhydrous methyl alcohol solvent.

8. The method of claim 1 and further including repeating the steps of titrating the homogenized sample of wood chips and determining the moisture content for additional amounts of the sample of wood chips to determine a mean and relative standard deviation of the moisture content of the sample.

9. The method of claim 1 and wherein the step of titrating the homogenized wood chips comprises adding a titrant to the solvent solution at a titration rate of between approximately 5 microliters/minute and approximately 10 milliliters/minute.

10. A method of determining moisture content in wood for use in a paper making process, comprising the steps of:

(a) freezing a representative sample of the wood so as to substantially fix moisture within the wood of the sample and minimize evaporation of moisture from the wood;

(b) placing a test sample of wood taken from the representative sample into a receiving vessel for a titration unit containing a solvent solution;

(c) adding a Karl Fischer reagent to the test sample in the solvent solution at a titration rate to titrate out the moisture within the test sample;

(d) detecting the presence of moisture in the test sample of wood in the solvent solution and continuing to add the reagent until the titration rate drops below a desired level; and (e) determining the moisture content of the test sample in view of test sample weight, amount of reagent added to the solvent solution to titrate out the moisture within the test sample and reagent concentration.

11. The method of claim 10 and wherein the step of freezing a representative sample of the wood comprises applying liquid nitrogen to the sample.

12. The method of claim 10 and further including homogenizing the test sample before placing the test sample in the solvent solution.

13. The method of claim 10 and further including repeating steps (b)–(e) to perform multiple tests to establish a mean moisture content and relative standard deviation of the moisture content of the wood.

14. The method of claim 10 and further comprising the steps of calibrating a moisture analyzer for a wood chip digester according to the moisture content determined for the test sample and monitoring the wood chips fed to the digester with the calibrated moisture analyzer to monitor the moisture content of the wood chips in real time to control operation of wood chip digester.

15. The method of claim 10 and wherein the step of adding the reagent comprises adding the reagent at a titration rate of between approximately 5 microliters and approximately 10 milliliters.

16. The method of claim 10 and further including the step of standardizing the reagent concentration, including the steps of adding a measured amount of a moisture standard material having a known moisture to the solvent solution, dispense the reagent into the solvent solution to titrate the moisture out of the solution, and determining the reagent concentration based upon the amount of reagent dispensed to titrate the moisture standard material.

17. The method of claim 10 and wherein the reagent comprises a non-pyridine containing Karl Fischer reagent.

* * * * *